United States Patent [19]

Krimm et al.

[11] 4,059,638

[45] Nov. 22, 1977

[54] TRISPHENOL PROCESS

[75] Inventors: Heinrich Krimm; Erhard Tresper, both of Krefeld, Germany

[73] Assignee: Bayer Aktiengesellschaft, Germany

[21] Appl. No.: 660,876

[22] Filed: Feb. 24, 1976

[30] Foreign Application Priority Data

Feb. 28, 1975 Germany .............................. 2508709

[51] Int. Cl.² ...................... C07C 41/06; C07C 37/00
[52] U.S. Cl. .............................. 260/613 R; 260/619 B; 260/613 B; 260/619 A; 260/2 EP
[58] Field of Search ............ 260/619 B, 619 A, 613 R

[56] References Cited

U.S. PATENT DOCUMENTS

| | | | |
|---|---|---|---|
| 2,801,989 | 8/1957 | Farnham | 260/619 B X |
| 2,885,385 | 5/1959 | Farnham | 260/619 B X |
| 3,264,358 | 8/1966 | Webb et al. | 260/619 B |
| 3,412,047 | 11/1968 | Shriver | 260/619 B X |

*Primary Examiner*—Bernard Helfin
*Attorney, Agent, or Firm*—Connolly and Hutz

[57] ABSTRACT

New trisphenols and their preparation by reacting the diacyl compound of dimeric p-isopropenylphenol or of a polycarbonate with a phenol in the presence of a strong acid catalyst at temperatures between $-20°$ and $30°$ C.

3 Claims, No Drawings

TRISPHENOL PROCESS

This invention relates to new trisphenols based on p-isopropenylphenol and to a process for their preparation.

It is known that p-isopropenylphenol is converted into the dimers (I) and (II) in accordance with the following equation when mildly heated, or even at 25° C, if it is dissolved in a solvent.

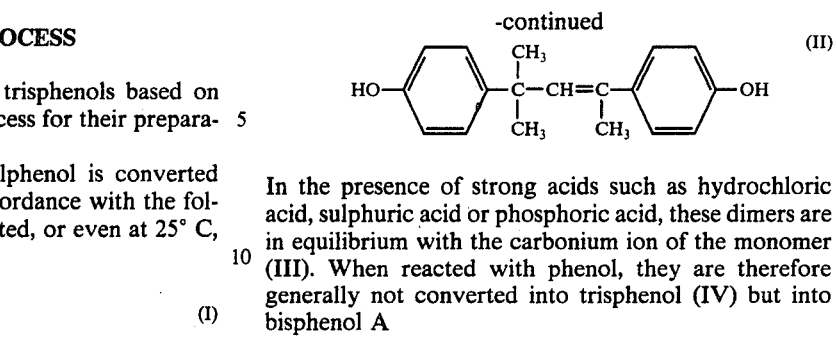

In the presence of strong acids such as hydrochloric acid, sulphuric acid or phosphoric acid, these dimers are in equilibrium with the carbonium ion of the monomer (III). When reacted with phenol, they are therefore generally not converted into trisphenol (IV) but into bisphenol A

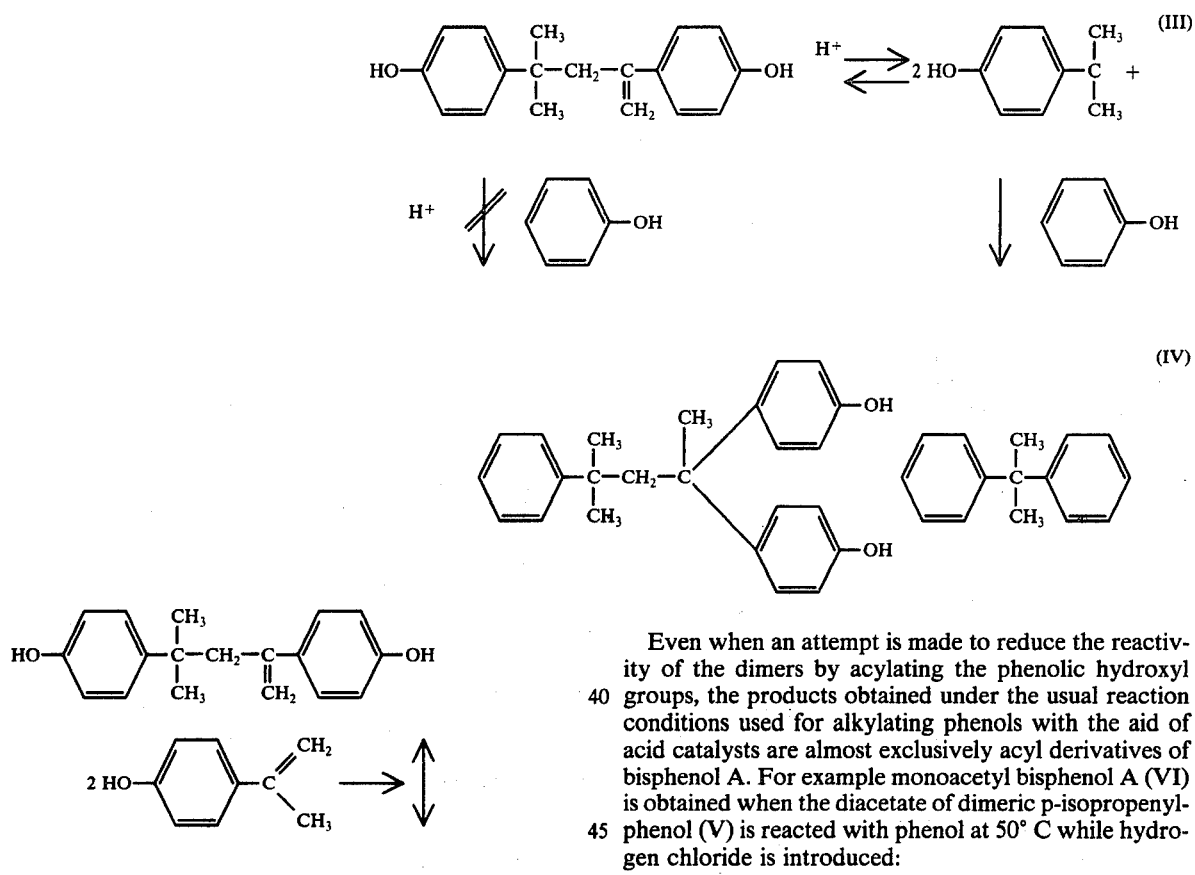

Even when an attempt is made to reduce the reactivity of the dimers by acylating the phenolic hydroxyl groups, the products obtained under the usual reaction conditions used for alkylating phenols with the aid of acid catalysts are almost exclusively acyl derivatives of bisphenol A. For example monoacetyl bisphenol A (VI) is obtained when the diacetate of dimeric p-isopropenylphenol (V) is reacted with phenol at 50° C while hydrogen chloride is introduced:

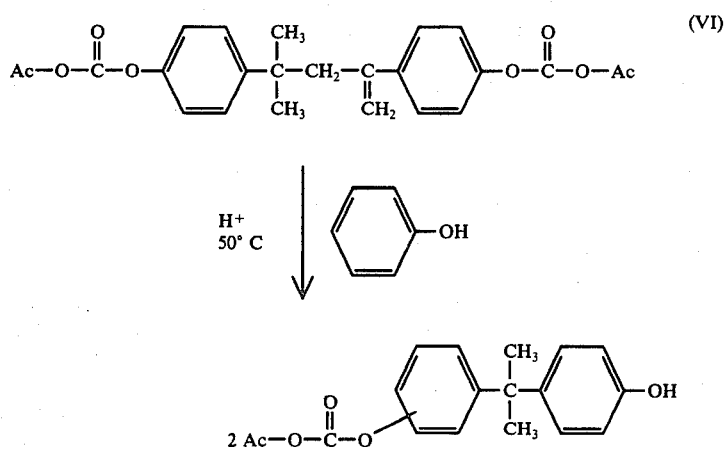

It has now surprisingly been found that the triphenol derivative (VII) is obtained when the reaction temperature is lowered:

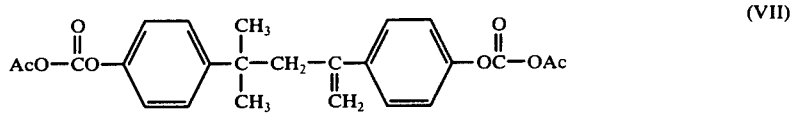

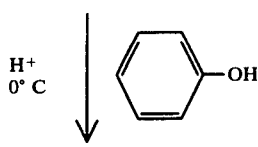

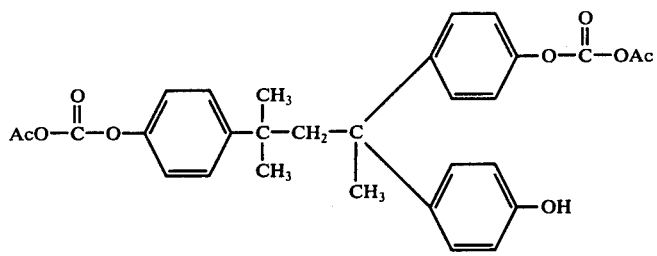

Trisphenol can easily be obtained from the diacetyl derivatives by saponification.

This invention therefore relates to new trisphenols of the general formula:

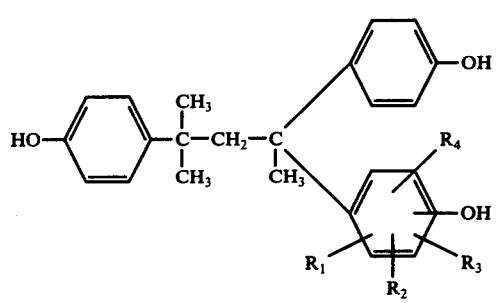

wherein $R_1$ to $R_4$, which may be the same or different, represent hydrogen, a $C_1$-$C_{12}$ alkyl group, halogen, OH or a $C_1$-$C_6$ alkoxy group.

Another object of this invention is a process for the preparation of these trisphenols, wherein the diacyl compounds of dimeric p-isopropenylphenol or the corresponding polycarbonates are reacted with phenols in the presence of strong acid catalysts, if desired in inert solvents, at temperatures between $-20°$ and $30°$ C and the resulting diacyl derivative of trisphenol is saponified in known manner.

The new trisphenols are preferably prepared by saturating a solution of the diacyl compound of the dimeric p-isopropenylphenols and the phenol with a vigorous stream of a hydrogen halide, distilling off the solvent and excess phenols, isolating the diacyl derivative of trisphenol from the residue by high vacuum distillation and then saponifying it in known manner.

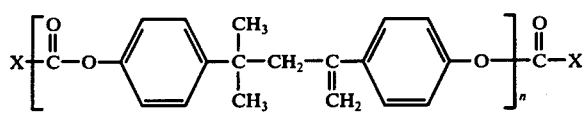

(VII)

-continued

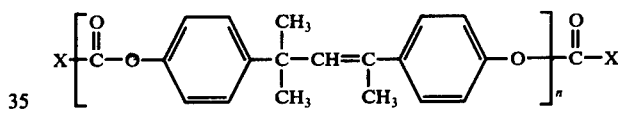

wherein X denotes a $C_1$ - $C_6$ aliphatic group, a phenyl group which may be substituted with halogen, preferably with chlorine or bromine, with a nitro group or with a $C_1$ - $C_4$ alkyl group; chlorine, a phenoxy group or a $C_1$ - $C_4$ alkoxy group, and $n$ represents an integer of from 1–50.

The following are given as examples: The diformyl, diacetyl, dipropionyl, dibutyryl, and dibenzoyl compounds of dimeric p-isopropenylphenols, the reaction products of dimeric p-isopropenylphenols wth phosgene and chlorocarbonic acid esters such as methyl chlorocarbonate, ethyl chlorocarbonate or phenyl chlorocarbonate, that is to say the dialkyl or diaryl carbonates of bis-chlorocarbonic acid esters, and the polycarbonate of dimeric p-isopropenyl phenols.

The above mentioned diacyl compounds can be prepared in known manner, for example by reacting the dimeric p-isopropenylphenols with the corresponding acid chlorides or anhydrides. When carrying out the reaction, the only precaution that is necessary is to ensure that the reaction medium is not too strongly acid, particularly when acid chlorides are used as acylating agents, because otherwise the dimeric p-isopropenylphenols are liable to be converted into trimers and polymers by unwanted side reactions.

Instead of using crystalline p-isopropenylphenol dimers the reaction may be carried out with resinous products of the kind obtained as a residue when phenol is distilled from the decomposition products of bisphenol A.

Suitable phenols for the reaction according to the invention are those of the general formula

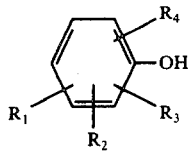

wherein $R_1$ to $R_4$, which may be the same or different, represent hydrogen, a $C_1$ – $C_{12}$ alkyl group, a halogen, preferably chlorine or bromine, OH or a $C_1$ to $C_6$ alkoxy group. The following are examples: Phenol, 0-, m- and p-cresol, o-, m- p-chlorophenol, 2,6-dichlorophenol, o-, m- and p-bromophenol, o-, m- and p-ethylphenol, o-,m- and p-propylphenol, o-, m- and p-isopropylphenol, o-, m- and p-butylphenol, o-, m- and p-isobutylphenol, o-, m- and p-tert.butylphenol, o-, m- and p-nonylphenol, o-, m- and p-dodecylphenol, 2,4-dimethylphenol, 3,4-dimethylphenol, 2,6-dimethylphenol, 2,6-diethylphenol, o-, m- and p-cyclohexylphenol, α-naphthol, β-naphthol, hydroquinone, resorcinol, pyrocatechol, hydroquinone monomethylether, resorcinol monomethylether and guaiacol.

Strong acid catalysts suitable for the reaction according to the invention include, for example, sulphuric acid, p-toluenesulphonic acid, methanesulphonic acid, concentrated hydrochloric acid, concentrated hydrobromic acid, boro trifluoride, phosphoric acid, cation exchangers such as sulphonated polystyrene and acid activated Fuller's earths, but the acid catalysts preferably used are hydrogen halides such as hydrogen chloride or hydrogen bromide, all used anhydrously.

The advantage of using anhydrous hydrogen halides is the ease with which the products can then be worked up. Non-volatile acids, by contrast, must be carefully washed out of the reaction product, if necessary after neutralisation, because they catalyse the decomposition of the reaction products at elevated temperatures whereas hydrogen halides can be removed at reduced pressure together with any solvents without any deleterious effect on the reaction products. In addition, hydrogen halides used as catalysts result in higher yields and give rise to fewer by-products. The quantity of catalyst used is between 0.01 and 1 mol per mol of diacyl compound of the dimeric p-isopropenylphenol. Hydrogen halides are preferably employed by saturating the reaction mixture with the gaseous acids.

Suitable solvents for the process include e.g. aliphatic or aromatic hydrocarbons, which may be halogenated if desired, such as benzene, toluene, cyclohexane, ligroin, methylene chloride, chloroform, carbon tetrachloride, ethylene chloride or chlorobenzene; cycloaliphatic or aliphatic ethers such as diethylether or dioxane or aliphatic esters of $C_2$ – $C_4$ aliphatic carboxylic acids, such as ethyl acetate or butyl acetate.

The reaction temperatures used are between −20° C and 30° C. As a general rule, the lower the reaction velocity of the phenol component used, the higher should be the reaction temperature used within the limits given above. Thus, for example, if phenol is used as reactant and hydrogen halide as catalyst, the most suitable reaction temperatures are between about −20° C and 10° C. If less reactive phenols are used, such as 2,6-dimethylphenol, reaction temperatures of between about 10° C and 30° C may suitably be used without affecting the yield. In special cases, it should not be too difficult, if following the guide lines indicated above, to find the most suitable temperature range by preliminary tests.

The phenols are suitably used in excess, i.e. in quantities of about 2 to 20 mol per mol of the diacyl compound of the dimeric isopropenylphenol.

The products of the process can be used for various technical purposes. Their reaction with epichlorohydrin yields highly heat resistant epoxide resins. Ethoxylation and propoxylation products of the new trisphenols are excellent textile additives and levelling agents for textile dyeing. The products are also suitable for the reversible cross-linking of polyurethanes.

EXAMPLE 1

(a) 2,4-Di-4'-acetoxyphenyl-4-methyl-pentene-1

A solution of 268 g (1 mol) of dimeric p-isopropenylphenol with a melting point of 131° C in 500 ml of acetic acid anhydride and 1 ml of pyridine is heated under reflux for 2 hours. Excess acetic acid anhydride is then removed at reduced pressure together with the glacial acetic acid formed, and the reaction product is distilled off as a viscous liquid at 178° to 182° C/0.08 Torr. $n_D^{20}$ = 1.549. Yield 342 g = 97% of theoretical.

(b) 2,2,4-Tri-4'-hydroxyphenyl-4-methyl-pentane

A stream of anhydrous hydrogen chloride is introduced into a solution of 176 g (0.5 mol) of the diacetyl compound prepared according to (a) above, in 470 g (5 mol) of phenol and 300 ml of methylene chloride at 0° C in the course of 6 hours until the solution is saturated. The hydrogen chloride, solvent and excess phenol are then removed by heating at reduced pressure to a reaction temperature of up to 200° C. 227 g of residue are obtained. High vacuum distillation yields 36 g of monoacetyl bisphenol A at between 195 ° to 210° C/0.04 Torr and 190 g of a 2,4-di-(4'-acetoxyphenyl)-2-(4''-hydroxyphenyl)-4-methyl-pentane fraction at 250° to 270° C/0.04 Torr. Yield: 85% of the theory.

By boiling in excess 2N sodium hydroxide solution until a clear solution is obtained, acidification with dilute acetic acid, dissolving the trisphenol in ethyl acetate and removing the solvent, trisphenol of the formula given below is obtained in the form of a hard resin. The melting point is between 150° and 152° C after recrystallisation from ethylene chloride.

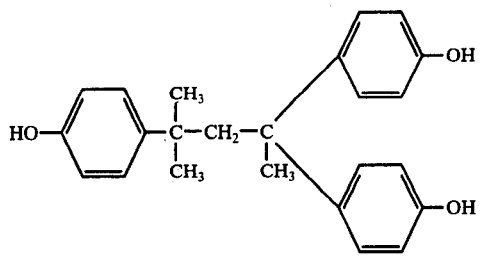

$C_{24}H_{26}O_3$ (362.5) Calculated: C, 79.53; H, 7.23; O, 13.24. Found: C, 79.42; H, 7.21; O, 13.51.

phenolic OH according to potentiometric titration: Calculated: 14.1. Found: 14.25.

(c) 140 g of 45% sodium hydroxide solution (1.575 mol) are introduced dropwise in the course of 2 hours into a solution of 182 g (½ mol) of the trisphenol prepared according to (b) above, in 700 g of epichlorohydrin at 95°–110° C with stirring while the water is continuously removed as an azeotropic mixture, using a water separator. Heating is then continued under reflux for a further 30 minutes until the reaction temperature reaches 118° C. Excess epichlorohydrin is then distilled off at reduced pressure until a reaction temperature of 140° C is reached. The residue is then dissolved in methylene chloride, the sodium chloride is filtered off in a suction filter operated under pressure and the solvent is removed, finally at reduced pressure, until the temperature in the reaction mixture has risen to 175° C. 242 g of a pale yellow resin having an epoxide number of 7.85% are obtained.

A melt of 68 g of this resin is mixed with 30 g of molten phthalic acid anhydride and the mixture is hardened to form a plate 4 mm in thickness by heating it to 160° C for 10 hours.

The dimensional stability under heat according to Martens is then 184° C. By contrast, a plate prepared in accordance with the above method from the reaction products of bisphenol A and epichlorohydrin has a dimensional stabiltiy according to Martens of only 132° C.

EXAMPLE 2

2,4-Di-(4'-hydroxyphenyl)-2-(4''-hydroxy-3''-methylphenyl)-4-methylpentane

A stream of anhydrous hydrogen chloride is introduced into a solution of 176 g (0.5 mol) of 2,4-di-4'-acetoxyphenyl-4-methylpentene-2 prepared from the dimeric p-isopropenylphenol having a melting point of 165° C according to Example 1(a) in 540 g of o-cresol and 200 ml of ethylene chloride at 0° C for 8 hours until the solution is saturated. The product is worked up as described in Example 1. After removal of the excess o-cresol at reduced pressure, 230 g of a resinous residue remain. This residue distils off almost completely at 255° to 270° C/0.04 Torr after a small amount of first runnings. Yield of 2,4-di-(4'-acetoxyphenyl)-2-(4''-hydroxy-3''-methylphenyl)-4-methyl-pentane: 200 g = 96% of theoretical.

The diacetyl compound is saponified by boiling it for several hours with excess 2N sodium hydroxide solution. The trisphenol is precipitated with 2N acetic acid, taken up in ethyl acetate, dehydrated over sodium sulphate and freed from solvent at reduced pressure. An amber coloured, hard resin is left behind. Melting point after recrystallisation from methylene chloride: 147° - 148° C.

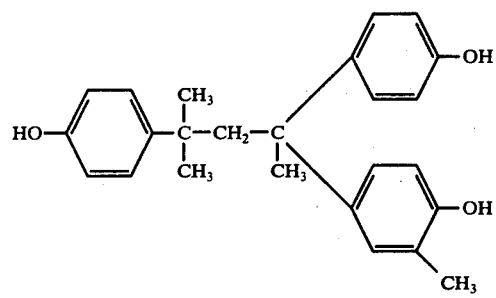

$C_{25}H_{28}O_3$ (376.5) Calculated: C, 79.75; H, 7.50; O, 12.75. Found: C, 79.61; H, 7.47; O, 12.90.
phenolic OH: Calculated: 13.5. Found 13.46.

EXAMPLE 3

2,4-Di-(4'-hydroxyphenyl)-2-(4'''-hydroxy-3'',5''-dimethylphenyl)-4-methylpentane A solution of 176 g (0.5 mol) of 2,4-di-4'-acetoxyphenyl-4-methylpentene-1 in 500 g of 2,6-dimethylphenol and 400 ml of methylene chloride is saturated with hydrogen chloride by passing anhydrous hydrogen chloride into it for 8 hours at 0° C and then for 8 hours at 20° C. The reaction mixture is then worked up as in Example 1. 232 g of resin are obtained as residue after removal of excess 2,6-dimethylphenol by distillation at reduced pressure. The main fraction of the reaction product is distilled off by high vacuum distillation at 260° to 275° C. 0.05 Torr. Yield of 2,4-di-(4'-acetoxyphenyl)-2-(4''-hydroxy-3'',5''-dimethylphenyl)-4-methyl pentane: 178 g = 75% of theoretical.

An amber coloured, hard resin is obtained after saponifying the reaction product in excess sodium hydroxide solution with the addition of 200 ml of methanol, precipitating the trisphenol with dilute hydrochloric acid, taking it up in ethyl acetate, dehydrating it over sodium sulphate and distilling off the solvent. Melting point after recrystallisation from methylene chloride: 98°- 100° C.

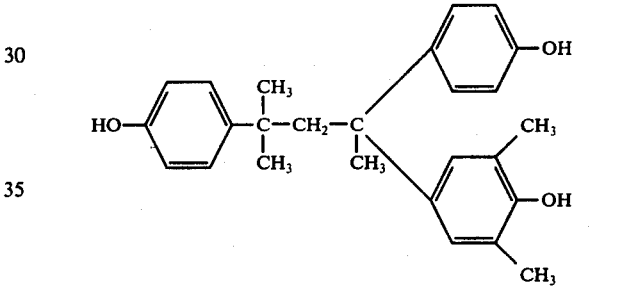

$C_{26}H_{30}O_3$ (390.5) Calculated; C, 79.96; H, 7.74; O, 12.29. Found: C, 79.78; H, 7.61; O, 12.42.
Phenolic OH: Calculated 13.0 Found 12.92

EXAMPLE 4

(a)
2,4-Di-(4'-chlorocarboxyphenyl)-4-methyl-pentene-1

300 g of phosgene are introduced into 1 l of anhydrous methylene chloride at −5° C and 268 g (1 mol) of dimeric p-isopropenylphenol which has a melting point of 131° C are introduced. 254 g (2.1 mol) of dimethylaniline are added dropwise in the course of one hour while the reaction mixture is cooled by means of a freezing mixture. The temperature is left to rise to room temperature and the reaction mixture is then heated under reflux for 2 hours. One third of the solvent is removed with excess phosgene at normal pressure. The residue is then cooled to 0° C and shaken twice with ice water, each time after the addition of 20 ml of concentrated hydrochloric acid. The product is dehydrated over sodium sulphate, the solvent is evaporated off and the residue is distilled at reduced pressure. The fraction containing the reaction product distils over as an almost colourless, viscous liquid at 180° to 188° C/0.07 Torr. Yield: 335 g = 85% of theoretical.

(b) 2,2,4-Tri-(4'-hydroxyphenyl)-4-methyl-pentane

Hydrogen chloride is introduced for 6 hours at 0° C into a solution of 78.6 g (0.2 mol) of the bischlorocarbonic acid ester of dimeric p-isopropenylphenol prepared according to (a) in 180 ml of toluene and 150 g of phenol. The solvent and excess phenol are removed at reduced pressure and the reaction product is dissolved in 400 ml of methanol, and 200 ml of concentrated sodium hydroxide solution are added dropwise. The reaction mixture is then diluted with an equal quantity of water and heated to reflux. The methanol is distilled off, 400 ml of toluene are added and the tris-phenol is precipitated with dilute hydrochloric acid. The solvent phase is washed with water, dehydrated over sodium sulphate and concentrated by evaporation. After removal of the excess phenol by distillation, a small amount of bisphenol A distils over, which is followed by the tris-phenol fraction which distils over at 270°–280° C/0.05 Torr. Melting point 150°–151° C (from methylene chloride). Yield: 48 g = 66% of theoretical.

EXAMPLE 5

(a) 2,4-Di-(4'-oxycarbophenoxyphenyl)-4-methylpentene-1

A solution of 189 g (0.2 mol) of phenylchloroformate in 500 ml of methylene chloride is run into a solution of 134 g (0.5 mol) of dimeric p-isopropenylphenol (melting point 131° C) in 1.8 l of 2N sodium hydroxide solution at room temperature. The reaction mixture is then stirred for 2 hours, the organic phase is washed with water and the solvent is removed at reduced pressure. A resinous product consisting of the bisphenyl carbonate of dimeric p-isopropenylphenol is obtained as residue. Yield: 234 g = 92% of theoretical. Melting point 77° C (from ethyl alcohol).

(b) 2,2,4-Tri-(4'-methyl-pentane

Anhydrous hydrogen chloride is introduced for 5 hours at 5° C into a solution of 127 g (0.25 mol) of the bisphenyl carbonate prepared according to (a) in 188 g (2 mol) of phenol and 400 ml of toluene. The solvent and excess phenol are removed at reduced pressure. The residue is saponified with a solution of 140 g of potassium hydroxide in 400 ml of methanol and 100 ml of water. The clear solution is diluted with 2 l of water and the tris-phenol is precipitated with 2N hydrochloric acid and taken up in ether. The ether residue is distilled off at reduced pressure. After removal of the bisphenol by distillation at 80° C/12 Torr and removal of small quantity of bisphenol A by distillation at 180° C/0.08 Torr, the trisphenol is left behind as a resin. Yield: 80 g = 88% of theoretical. After recrystallisation from methylene chloride, the melting point is 150° to 152° C.

We claim:

1. A process for the production of a trisphenol wherein a compound of the formula

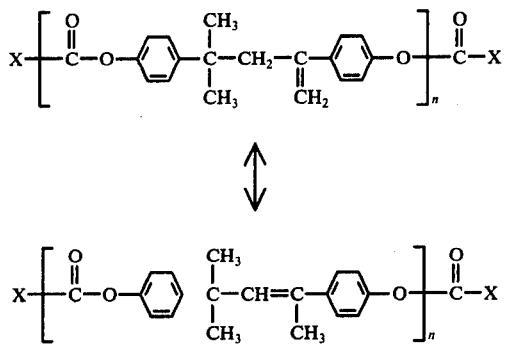

wherein: X represents a $C_1$–$C_6$ aliphatic group, a $C_1$–$C_4$ alkoxy group, a phenoxy group, a phenyl group optionally substituted by halogen, nitro or $C_1$–$C_4$ alkyl, or chlorine and n is an integer from 1 to 50, is reacted with a phenol selected from the group consisting of phenol, cresol, chlorophenol, 2,6-dichlorophenol, bromophenol, ethylphenol, propylphenol, isopropylphenol, butylphenol, isobutylphenol, tert.butylphenol, nonylphenol, dodecylphenol, 2,4-dimethylphenol, 3,4-dimethylphenol, 2,6-dimethylphenol, 2,6-diethylphenol, cyclohexylphenol, hydroquinone, resorcinol, pyrocatechol, hydroquinone monomethylether, resorcinol monomethylether and guaiacol in the presence of an acid catalyst at a temperature of from −20° to 30° C. and the resulting acyl derivative is saponified to form the trisphenol.

2. A process as claimed in claim 1, wherein the acid catalyst is a hydrogen halide.

3. A process as claimed in claim 1, wherein the reaction is carried out in an inert solvent.

* * * * *